(12) United States Patent
Nishino (10) Patent No.: US 8,654,925 B2
(45) Date of Patent: Feb. 18, 2014

(54) RADIATION IMAGING CONTROL APPARATUS AND OPERATION CONTROL METHOD OF THE SAME

(75) Inventor: Naoyuki Nishino, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 302 days.

(21) Appl. No.: 13/216,560

(22) Filed: Aug. 24, 2011

(65) Prior Publication Data

US 2012/0051521 A1    Mar. 1, 2012

(30) Foreign Application Priority Data

Aug. 27, 2010    (JP) .................................. 2010-190208

(51) Int. Cl.
*H05G 1/64*    (2006.01)

(52) U.S. Cl.
USPC ........................................ 378/98.5; 378/115

(58) Field of Classification Search
USPC ............ 378/91, 98, 98.2, 98.5, 114, 115, 117
See application file for complete search history.

(56) References Cited

U.S. PATENT DOCUMENTS

| 6,859,521 B2 * | 2/2005 | Spahn ........................... 378/117 |
| 8,376,612 B2 * | 2/2013 | Takae et al. .................. 378/198 |
| 8,419,276 B2 * | 4/2013 | Oda et al. ..................... 378/198 |

FOREIGN PATENT DOCUMENTS

| JP | 2003-334185 A | 11/2003 |
| JP | 2006-43273 A | 2/2006 |
| JP | 2008073121 A | 4/2008 |
| JP | 2010-119485 A | 6/2010 |

OTHER PUBLICATIONS

Notification of Grounds for Rejection dated Dec. 17, 2013, issued in Japanese Patent Application No. 2010-190208.

* cited by examiner

*Primary Examiner* — Jurie Yun
(74) *Attorney, Agent, or Firm* — Sughrue Mion, PLLC (57) ABSTRACT

A movably constructed radiation imaging control apparatus which receives a predefined operational instruction for radiation imaging to output a control signal for the radiation imaging according to the received operational instruction and displays radiological examination information. The apparatus includes a location information obtaining unit for obtaining location information capable of identifying a location of the apparatus and a function restriction unit for restricting a part of a function of the apparatus if the location identified by the location information obtained by the location information obtaining unit is a location other than a predetermined location.

14 Claims, 8 Drawing Sheets

RADIATION IMAGING CONTROL APPARATUS AND OPERATION CONTROL METHOD OF THE SAME

BACKGROUND OF THE INVENTION

1. Field of the Invention

The present invention relates to a radiation imaging control apparatus that receives a predefined operational instruction for radiation imaging to output a control signal for the radiation imaging and displays radiological examination information. The invention also relates to an operation control method of the same.

2. Description of the Related Art

Recently, digitization and size-reduction of radiation imaging devices have been in progress and medical carts provided with a semiconductor radiation image detector and a console having a monitor for displaying a radiation image obtained by the radiation image detector are proposed as described, for example, in Japanese Unexamined Patent Publication Nos. 2003-334185 and 2010-119485. Such medical carts allow a radiation image obtained in a patient room or the like to be displayed on the monitor for verification on the spot.

The console has functions to manage and register personal data of patients, to view radiation images of patients, and to enlarge the obtained image other than the function to display the obtained image.

At the visiting radiation imaging site, however, the monitor of the console is exposed to many unrelated persons. Radiological examination information displayed on the monitor may include personal information of the patient so that sufficient care must be taken to protect the personal information.

In a case where a radiologist visits alone for taking a radiation image of a patient, the radiologist needs to concentrate on positioning the patient for the radiation imaging and can not pay attention to the security of information displayed on the monitor of the console, thereby causing the information to be unintentionally peeped by unrelated bystanders or to be altered with harmful intent.

Consequently, in order to prevent the leakage of personal information, a mobile radiation imaging device that allows switching, by the operation of the operator, between display and non-display of personal information is proposed as described, for example, in Japanese Unexamined Patent Publication No. 2006-043273.

The device described in Japanese Unexamined Patent Publication No. 2006-43273, however, requires the operator to purposely switch the display and if the switching is omitted, the personal information is leaked after all.

The medical cart may be used not only at the visiting medical site but also in a radiation imaging room. In such a case, it is not necessary to restrict the display contents as no unrelated person is present in the room other than authorized personnel and the operator needs to switch the display again.

In view of the circumstances described above, it is an object of the present invention to provide a radiation imaging control apparatus capable of restricting the display of personal information at a visiting medical site while allowing required examination information to be fully displayed at a predetermined location, such as a radiation imaging room or the like, without requiring an extra effort of the operator. It is a further object of the present invention to provide an operation control method of the radiation imaging control apparatus.

SUMMARY OF THE INVENTION

An operation control method of a radiation imaging control apparatus of the present invention is an operation control method for a radiation imaging control apparatus which is constructed movably and includes a control unit for receiving a predefined operational instruction for radiation imaging to output a control signal for the radiation imaging according to the received operational instruction and a display unit for displaying radiological examination information, wherein:

the apparatus obtains location information capable of identifying a location of the apparatus; and a part of a function of the apparatus is restricted if the location identified by the obtained location information is a location other than a predetermined location.

A radiation imaging control apparatus of the present invention is an apparatus which is constructed movably and includes a control unit for receiving a predefined operational instruction for radiation imaging to output a control signal for the radiation imaging according to the received operational instruction and a display unit for displaying radiological examination information, wherein the apparatus comprises:

a location information obtaining unit for obtaining location information capable of identifying a location of the apparatus; and a function restriction unit for restricting a part of a function of the apparatus if the location identified by the location information obtained by the location information obtaining unit is a location other than a predetermined location.

In the radiation imaging control apparatus of the present invention, the location information obtaining unit may be a unit that performs wireless communication with a predetermined access point and obtains a communication status of the wireless communication as the location information.

Further, the location information obtaining unit may be a unit that receives the control signal outputted from the control unit and obtains type information for a radiation image detector that detects a radiation image.

Still further, the location information obtaining unit may be a unit that receives the control signal outputted from the control unit and obtains quantity information for a radiation image detector that detects a radiation image.

Further, the apparatus may include a position detection unit for detecting a location of the apparatus and the location information obtaining unit may be a unit that obtains the location detected by the position detection unit as the location information.

Still further, the apparatus may include a travel distance information obtaining unit for obtaining a travel distance of the apparatus and the position detection unit may be a unit that performs the detection of a location of the apparatus in the case where the travel distance becomes greater than or equal to a predetermined value.

Further, the function restriction unit may be a unit that restricts display of a portion of the radiological examination information to be displayed on the display unit.

Still further, the function restriction unit may be a unit that restricts display of information related to personal information included in the radiological examination information to be displayed on the display unit.

Further, the function restriction unit may be a unit that restricts display of a radiation image included in the radiological examination information to be displayed on the display unit.

Still further, the function restriction unit may be a unit that restricts display of a radiation image for use in radiology reading included in the radiological examination information to be displayed on the display unit.

Further, the function restriction unit may be a unit that restricts display of a radiation image obtained in the past included in the radiological examination information to be displayed on the display unit.

Still further, the function restriction unit may be a unit that restricts display of a radiation image included in the radiological examination information to be displayed on the display unit other than a most recently obtained radiation image.

A radiation image taking system of the present invention is a system that includes the radiation imaging control apparatus described above, a radiation source for emitting radiation based on a control signal outputted from the radiation imaging control apparatus, and a radiation image detector for receiving radiation emitted from the radiation source and transmitted through a subject to detect a radiation image, wherein the apparatus is constructed movably.

According to the radiation imaging control apparatus of the present invention, location information capable of identifying a location of the apparatus is obtained and a part of a function of the apparatus is restricted if the location identified by the obtained location information is a location other than a predetermined location. This allows a function to display personal information of a patient to be restricted automatically without requiring an extra effort of the operator in the case where the radiation imaging control apparatus is placed, for example, in a visiting radiation imaging site, such as a patient room, other than the radiation imaging room, whereby leakage of personal information of a patient may be prevented.

Further, in the case where the apparatus is returned to a predetermined location, such as the radiation imaging room or the like, the restriction of the function may be released automatically, without bothering the operator to perform display switching, whereby all items of radiological examination information required by the operator may be provided.

DESCRIPTION OF THE PREFERRED EMBODIMENTS

Figure 1:
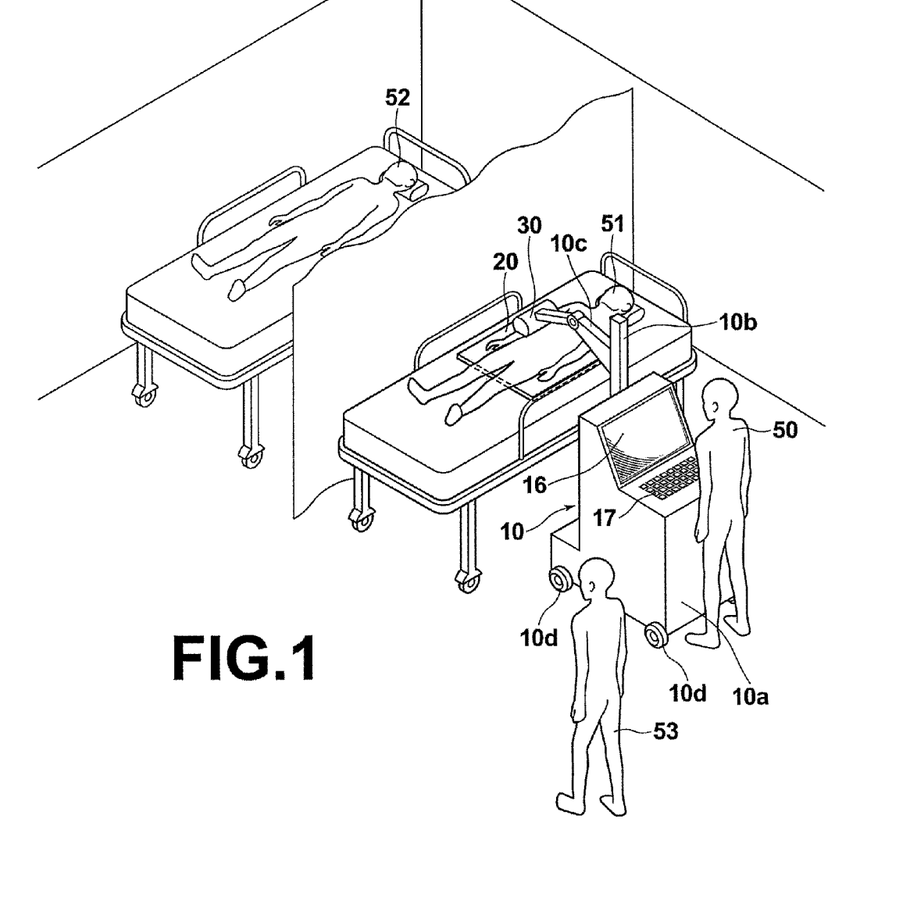
FIG. 1 illustrates a radiation image taking system that employs an embodiment of the radiation imaging control apparatus of the present invention placed in a patient room.

Hereinafter, a radiation image taking system that employs an embodiment of the radiation imaging control apparatus of the present invention will be described with reference to the accompanying drawings. FIG. 1 illustrates a state of a patient room in which the radiation image taking system of the present embodiment is placed.

The radiation image taking system of the present embodiment includes console 10 for receiving a predefined operational instruction for radiation imaging to output a control signal for the radiation imaging, radiation source 30 provided to console 10, and radiation detection cassette 20 which includes a built-in radiation image detector for detecting radiation emitted from radiation source 30 and transmitted through patient 51 to detect a radiation image of patient 51. Signals are exchanged between console 10 and radiation detection cassette 20 by wireless communication.

Radiation source 30 is provided to console 10 via support 10b and arm section 10c. Arm section 10c is movable in up-down directions with respect to support 10b and extensible. This allows radiation source 30 to be moved to a desired position according to a target region of patient 51 for radiation imaging.

Main body 10a of console 10 includes display unit 16 for displaying radiological examination information and input unit 17 for receiving radiation imaging order information which includes patient information and an imaging condition, with four wheels 10d attached at the bottom to movably support main body 10a.

Figure 2:
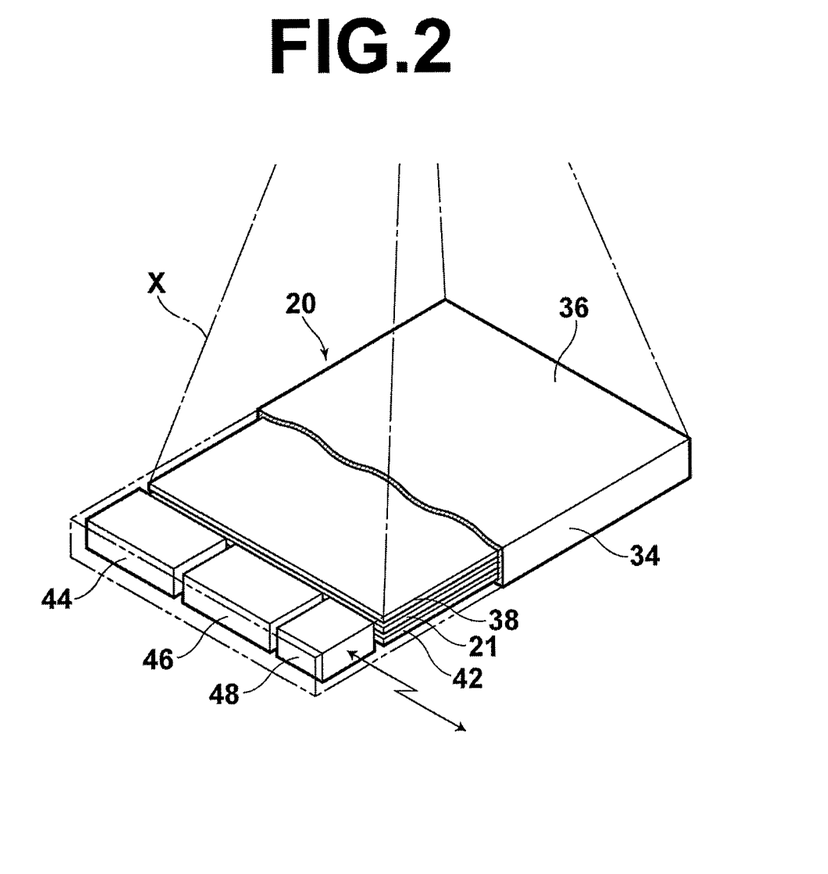
FIG. 2 illustrates an internal configuration of the radiation detection cassette shown in FIG. 1.

FIG. 2 illustrates an internal configuration of radiation detection cassette 20. Radiation detection cassette 20 includes casing 34 made of a material that transmits radiation X. Casing 34 includes therein, from irradiation surface 36 on which radiation X is directed, in the order of grid 38 for removing scattered rays of radiation X scattered by patient 51, radiation image detector 21 for detecting radiation X transmitted through patient 51 to detect a radiation image of patient 51, and lead plate 42 for absorbing back scattering of radiation X.

Casing 34 further includes therein battery 44 which is the power source of radiation detection cassette 20, cassette control unit 46 for drive controlling radiation image detector 21 using power supplied from battery 44, and cassette transceiver 48 for transmitting a radiation image signal read out from radiation image detector 21 and the like to console 10 as a wireless communication signal and receiving a control signal and the like outputted from console 10.

Preferably, a lead plate or the like is provided for cassette control unit 46 and cassette transceiver 48 on the side of irradiation surface 36 in order to prevent damage from radiation X.

Radiation image detector 21 is a detector that allows repeated radiation image recording and reading and, as radiation image detector 21, a so-called direct type radiation image detector that generates a charge by directly receiving radiation or a so-called indirect type radiation image detector that first converts radiation to visible light and then converts the visible light to a charge signal. As for the radiation image signal readout method, a so-called TFT (thin film transistor) readout method in which a radiation image signal is read out by ON/OFF switching thin film transistors and a so-called optical readout method in which a radiation image signal is read out by illuminating readout light are preferably used, but other method may also be used.

Figure 3:
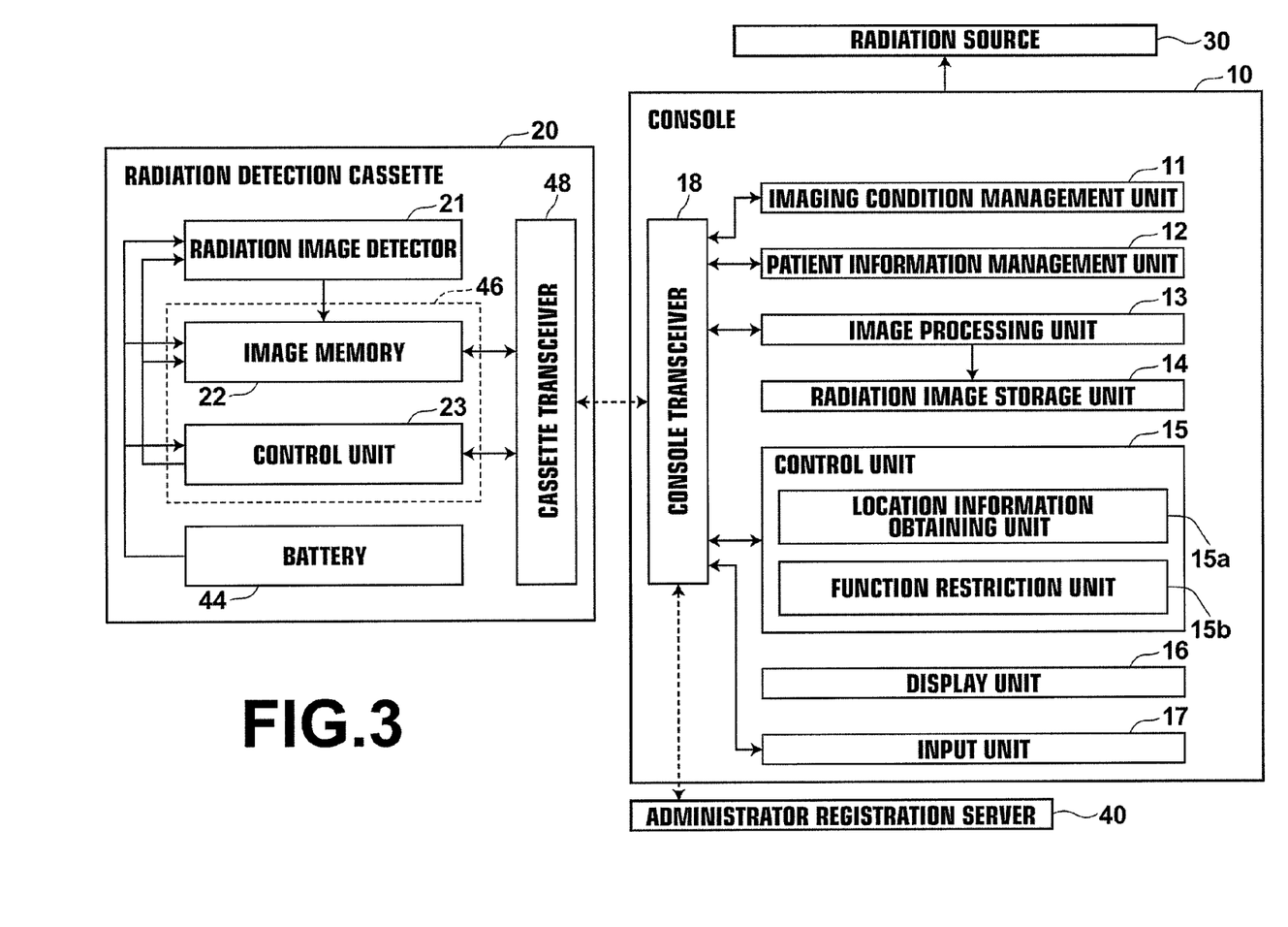
FIG. 3 is a block diagram of the radiation image taking system, schematically illustrating a configuration thereof.

FIG. 3 is a block diagram illustrating an internal configuration of the radiation image taking system constituted by console 10, radiation detection cassette 20, and radiation source 30.

Radiation source 30 is a source that emits radiation toward patient 51 in response to a control signal based on an imaging condition or a control signal of radiation imaging start instruction outputted from console 10.

As described above, radiation detection cassette 20 includes radiation image detector 21, battery 44, cassette control unit 46, and cassette transceiver 48.

Cassette control unit 46 includes image memory 22 for storing a radiation image signal read out from radiation image detector 21 and control unit 23 for controlling the operation of cassette transceiver 48.

Control unit 23 controls reading of radiation image signals from radiation image detector 21 and image memory 22, in addition to transmitting various types of information within radiation detection cassette 20, such as an operation status of radiation image detector 21, to console 10 via cassette transceiver 48 and receiving various types of control signals for radiation detection cassette 20 from console 10 via cassette transceiver 48.

Control signals outputted from console 10 to radiation detection cassette 20 includes, for example, a cassette ready signal, a radiation imaging start signal, a radiation imaging end signal, and the like. The cassette ready signal is a signal for constantly resetting radiation image detector 21 so as not to accumulate unnecessary charges when the detector is moved to an imaging standby mode. The radiation imaging start signal is a control signal to cause radiation image detector 21 to become a charge accumulation mode, and the radiation imaging end signal is a control signal to cause radiation image detector 21 to become charge signal readout mode from the charge accumulation mode.

Console 10 includes console transceiver 18 for wireless communication with radiation detection cassette 20 and radiation source 30 to transmit and receive necessary information, including a radiation image signal, imaging condition management unit 11 for managing imaging conditions required for radiation imaging, patient information management unit 12 for managing patient information of an imaging target, patient 51, image processing unit 13 for performing image processing on the radiation image signal transmitted from radiation detection cassette 20, and radiation image storage unit 14 for storing the processed radiation image signal. Console 10 further includes control unit 15 for outputting various types of control signals to radiation detection cassette 20 and receiving various types of information, such as operational status of radiation image detector 21 and the like, from radiation detection cassette 20, display unit 16 for displaying radiological examination information, such as an imaging condition, patient information, and radiation image signal outputted from radiation detection cassette 20, and input unit 17 for receiving input of imaging order information, including imaging conditions and imaging target patient information.

As shown in FIG. 3, control unit 15 of console 10 includes location information obtaining unit 15a for obtaining location information capable of identifying a location of console 10 and function restriction unit 15b for restricting a certain function of console 10 in the case where a location identified by the location information obtained by location information obtaining unit 15a is a location other than a predetermined location.

Location information obtaining unit 15a of the present embodiment performs wireless communication with administrator registration server 40 installed at a location other than the patient room, such as the radiation imaging room or radiation imaging preparation room, via console transceiver 18 to obtain a communication status of the wireless communication as the location information and outputs the obtained information to function restriction unit 15b.

Based on the communication status between console 10 and administrator registration server 40 outputted from location information obtaining unit 15a, function restriction unit 15b determines whether or not console 10 is in a place other than the radiation imaging room or radiation imaging preparation room and restricts display of a portion of radiological examination information displayed on display unit 16 of console 10 if console 10 is in a place other than the radiation imaging room or radiation imaging preparation room. The method of determining whether or not console 10 is in a place other than the radiation imaging room or radiation imaging preparation room and radiological examination information to be subjected to the display restriction will be described later.

Administrator registration server 40 shown in FIG. 3 is normally installed in the radiation imaging room or radiation imaging preparation room and includes information of administrators authorized to use console 10. The server 40 receives a response request signal which includes operator information of console 10 outputted from location information obtaining unit 15a of console 10, determines whether or not the operator included in the response request signal is a registered administrator, and transmits a response signal, including a result of the determination, to location information obtaining unit 15a of console 10.

An operation of the radiation image taking system of the present embodiment will now be described with reference to the flowchart of FIG. 4.

First, console 10 is placed in a given location, such as a patient room or a radiation imaging room, by a doctor or a radiological technologist (hereinafter, "operator") at the time of carrying out visiting medical service or radiation imaging and the location is detected (S10). Now, detection of the location of console 10 will be described in detail with reference to the flowchart of FIG. 5.

Figure 5:
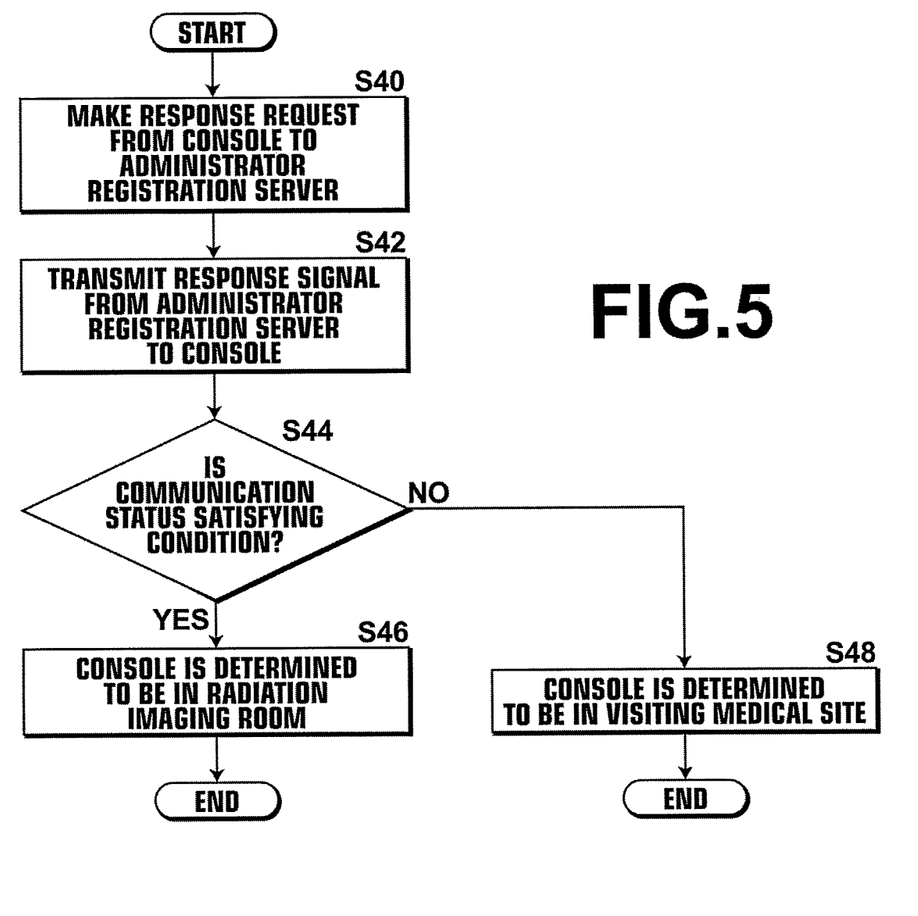
FIG. 5 is a flowchart illustrating an example method of identifying the location of the console.

As shown in FIG. 5, operator information is inputted by the operator using input unit 17 of console 10 and the inputted operator information is outputted to administrator registration server 40 installed in the radiation imaging room or radiation imaging preparation room via console transceiver 18 of console 10 as a response request signal (S40).

The response request signal, including operator information, outputted from console 10 is received by administrator registration server 40, and administrator registration server 40 determines whether or not the operator included in the response request signal is a registered administrator. Then, administrator registration server 40 transmits a response signal, including a results of the determination as to whether or not the inputted operator is a registered administrator, to console 10 (S42).

The response signal outputted from administrator registration server 40 is received by location information obtaining unit 15a via console transceiver 18 of console 10. Then, location information obtaining unit 15a confirms whether or not the communication status with administrator registration server 40 satisfies a predetermined condition. More specifically, a determination is made, in the present embodiment, as to whether or not strength of the received response signal is greater than or equal to a predetermined value (S44).

If the strength of the received response signal is greater than or equal to the predetermined value, location information obtaining unit 15a determines that console 10 is in the radiation imaging room or radiation imaging preparation room (S46), while if the strength of the response signal is less than the predetermined value, console 10 is determined to be in a visiting medical site other than the radiation imaging room or radiation imaging preparation room (S48).

A result of the determination of the location information obtaining unit 15a is outputted to function restriction unit 15b, and function restriction unit 15b resets a function restriction flag if console 10 is determined to be in the radiation imaging room or radiation imaging preparation room, while if console 10 is determined to be in a visiting medical site other than the radiation imaging room or radiation imaging preparation room, the function restriction flag is set. When the function restriction flag is set, display of a portion of radiological examination information to be displayed on display unit 16 of console 10 is restricted, which will be described later in detail.

In the present embodiment, a determination is made as to whether or not the communication status between console 10 and administrator registration server 40 satisfies a predetermined condition using the response signal strength, but the determination may be made using, for example, communication quality. More specifically, for example, a bit error rate of the response signal may be obtained, and console 10 may be determined to be in the radiation imaging room or radiation imaging preparation room if the value is within a predetermined value, while if the value is greater than the predetermined value, the console 10 may be determined to be in a visiting medical site other than the radiation imaging room or radiation imaging preparation room.

Further, if the response signal from administrator registration server 40 is a signal indicating that the operator included in the information outputted from console 10 is not registered in administrator registration server 40 in advance, console 10 may be made not to accept any operational instruction.

Figure 4:
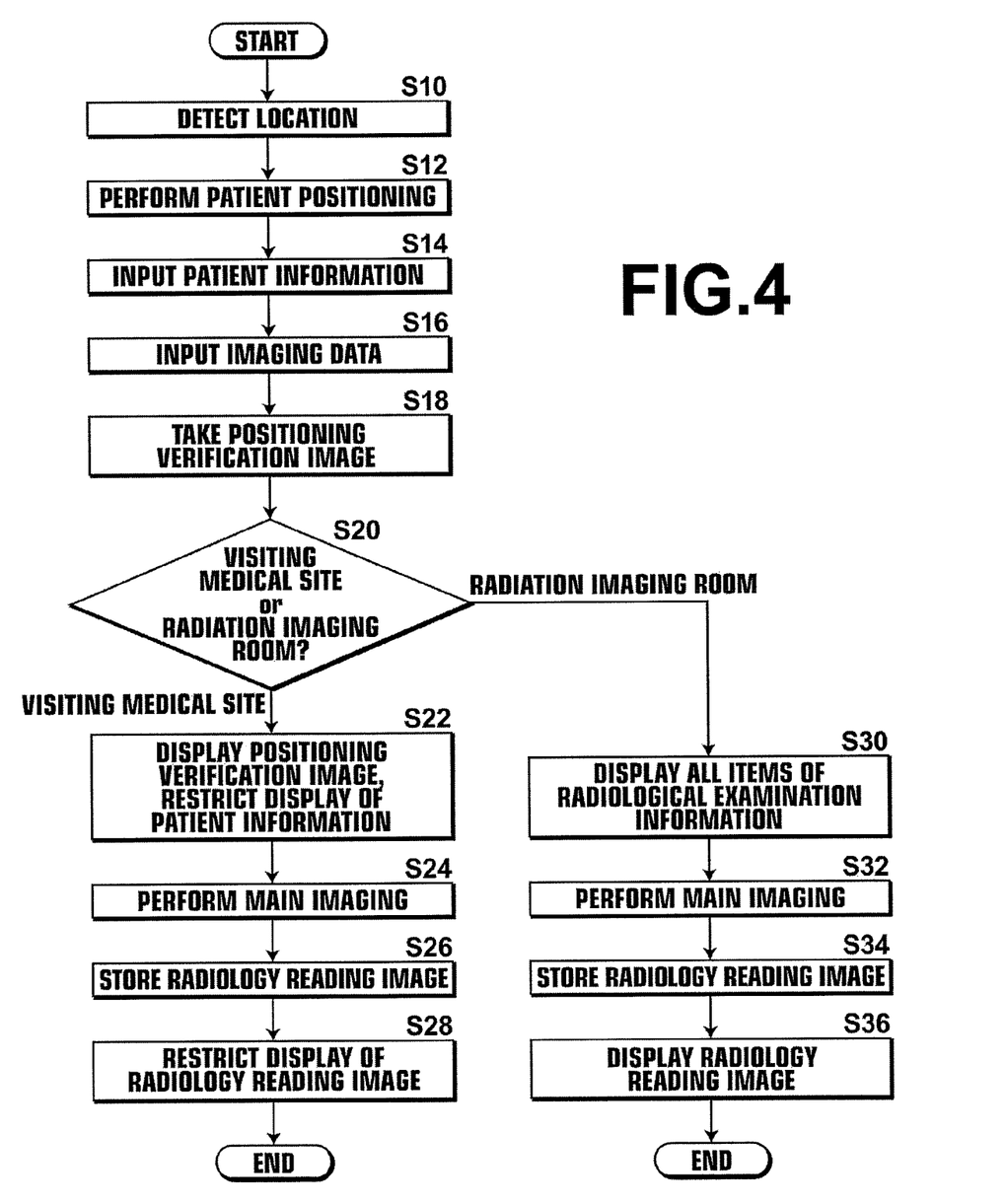
FIG. 4 is a flowchart describing an operation of the radiation image taking system that employs an embodiment of the radiation imaging control apparatus of the present invention

Now referring again to the flowchart of FIG. 4, after detection of the location is performed in the manner described above, radiation detection cassette 20 is placed at a prescribed location between the patient and imaging platform with irradiation surface 36 facing radiation source 30 and the patient is set in place (S12).

Thereafter, the operator inputs patient information of the imaging target patient and imaging order information using input unit 17 of console 10, and the patient information is registered in patient information management unit 12 while imaging order information is registered in imaging condition management unit 11 (S14, S16). Patient information may include, for example, age, gender, disease name, history of disease, name of administered drug, allergy information, pregnancy information, face photograph, photograph of affected area, such as a skin disease, and the like, but not all of these items need to be inputted and some of them may be set in patient information management unit 12 in advance. Imaging order information may include, for example, imaging procedure, tub voltage, tube current, and emission time for exposing the imaging region of the patient with an appropriate dose of radiation, and the like. Imaging order information is not restricted to those described above and may include any information as long as it is necessary for radiation imaging.

Then, a start instruction to start imaging for verifying positioning of the patient is inputted by the operator using input unit 17 of console 10 and a predetermined dose of radiation is emitted from radiation source 30 in response to the input, thereby imaging for verifying the positioning is performed prior to main radiation imaging (S18).

More specifically, radiation source 30 is controlled based on an imaging condition inputted by the operator and a predetermined dose of radiation determined according to the imaging condition is emitted to the patient.

After scattered rays are removed by grid 38 of radiation detection cassette 20, radiation transmitted through the patient is incident on radiation image detector 21 where the radiation is subjected to photoelectric conversion and stored as a charge signal.

After the emission of radiation X performed in the manner described above is completed, the charge signal stored in radiation image detector 21 is read out by control unit 23, sampled by a sample and hold circuit, converted to a digital signal by an A/D converter, and temporarily stored in image memory 22. Here, the positioning verification image signal can be a low resolution image signal and, for example, binning readout is performed.

When an amount of radiation image signals required for unit transmission are accumulated in image memory 22, control unit 23 serially reads out the amount of radiation image signals for the unit transmission from image memory 22 and outputs to cassette transceiver 48.

Then, cassette transceiver 48 modulates and transmits inputted radiation image signal to console 10 as a wireless communication signal.

The modulated signal transmitted to console 10 is demodulated by console transceiver 96 as a radiation image signal. The radiation image signal will be subjected to predetermined image processing in image processing unit 13 and outputted to display unit 16 with the imaging condition and patient information. Here, a determination is made by function restriction unit 15b whether or not the function restriction flag is set. That is, a determination is made whether console 10 is in a visiting medical site, or in the radiation imaging room or radiation imaging preparation room (S20).

In the case where a determination is made by function restriction unit 15b that console 10 is in a visiting medical site like that shown in FIG. 1, function restriction unit 15b restricts display of a portion of the radiological examination information to be displayed on display unit 16 (S22).

The reason for the display restriction is that, for example, in the visiting medical site shown in FIG. 1, the operator is required to move back and forth between console 10 and the patient, and the operator may leave from the screen of console 10.

In such a case, as shown in FIG. 1, visitor 53 visiting the neighboring patient 52 or another person other than medical staff may pass by console 10 and radiological examination information of patient 51 displayed on console 10 may be peeped. Consequently, display restriction is implemented in console 10 of the present invention in order to prevent leakage of personal information of patient.

More specifically, in the present embodiment, a low resolution positioning verification image, which does not lead to serious leakage of personal information, and an imaging condition, which is the information required by the operator for main imaging, are displayed on display unit 16 without any display restriction, while patient information which may lead to serious leakage of personal information is controlled and not displayed on display unit 16.

Figure 6:
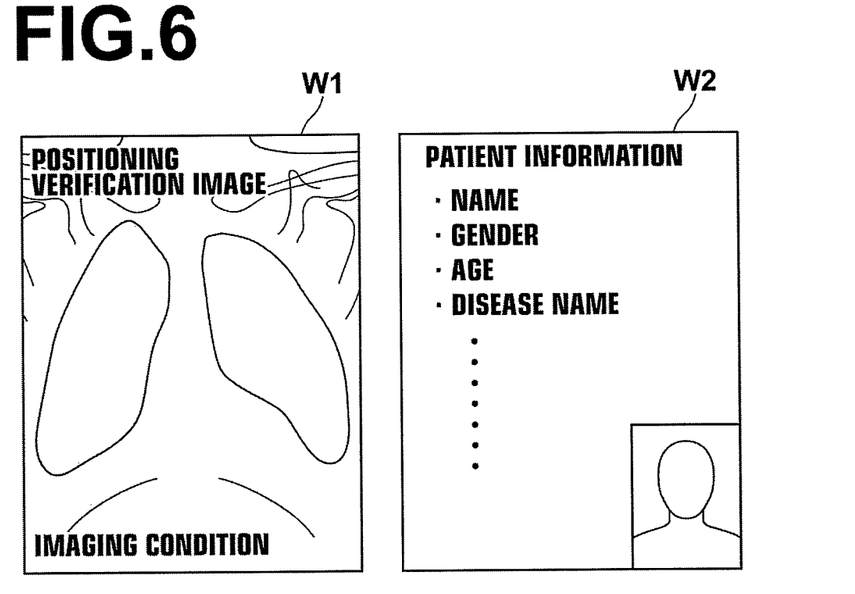
FIG. 6 illustrates a state in which all items of radiological examination information are displayed.
Figure 7:
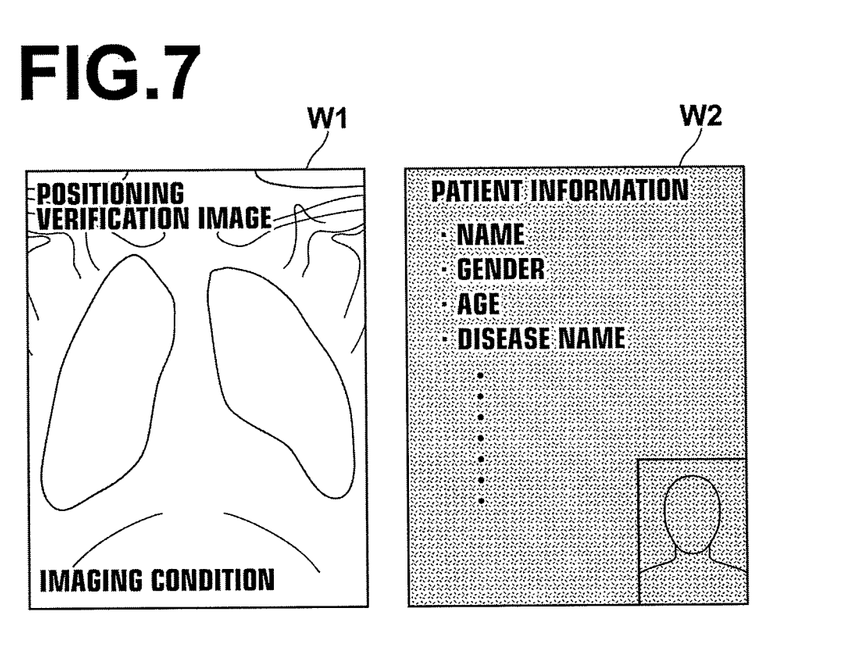
FIG. 7 illustrates a state in which display of personal information of a patient is restricted.
Figure 8:
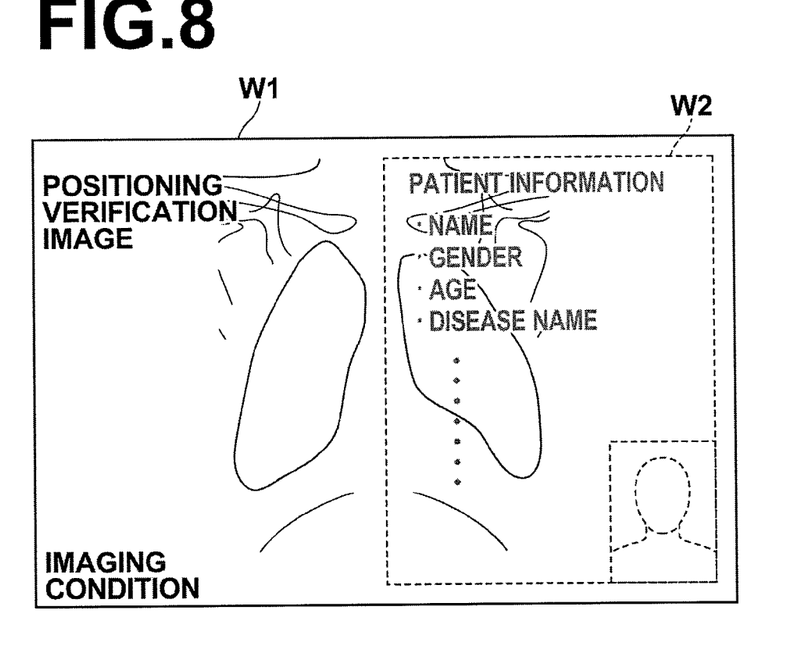
FIG. 8 illustrates another example state in which display of personal information of a patient is restricted.

FIG. 6 illustrates a screen in which all items of radiological examination information are displayed without the aforementioned display restriction, while FIG. 7 illustrates a screen in which the aforementioned patient information is in display restriction. Window W1 of the screen displays a positioning verification image and an imaging condition, while window W2 of the screen displays patient information. As for the method of restricting the display of patient information, a method that hides window W2, as illustrated in FIG. 7, or a method that enlarges window W1 to cover window W2, as illustrated in FIG. 8, may be employed.

Then, the positioning verification image and imaging condition displayed in the manner described above are confirmed by the operator and main imaging is performed after the imaging condition or positioning of the patient is changed as required (S24).

More specifically, a start instruction to start main imaging is inputted by the operator using input unit 17 of console 10 and, in response to the input, radiation source 30 is controlled based on the imaging condition, thereby a predetermined dose of radiation according to the imaging condition is emitted to the patient.

After scattered rays are removed by grid 38 of radiation detection cassette 20, radiation transmitted through the patient is incident on radiation image detector 21 where the radiation is subjected to photoelectric conversion and stored as a charge signal.

After the emission of radiation X performed in the manner described above is completed, the charge signal stored in radiation image detector 21 is read out by control unit 23, sampled by a sample and hold circuit, converted to a digital signal by an A/D converter, and temporarily stored in image memory 22.

When an amount of radiation image signals required for unit transmission are accumulated in image memory 22, control unit 23 serially reads out the amount of radiation image signals for the unit transmission from image memory 22 and outputs to cassette transceiver 48.

Then, cassette transceiver 48 modulates and transmits inputted radiation image signal to console 10 as a wireless communication signal.

The modulated signal transmitted to console 10 is demodulated by console transceiver 96 as a radiation image signal and the radiation image signal is subjected to predetermined image processing in image processing unit 13 and stored in storage unit 14 with patient information of patient 51 registered in patient information management unit 12 being related thereto (S26).

Thereafter, the image signal for radiology reading obtained by the main imaging and stored in radiation image storage unit 14 in the manner described above will be read out by control unit 15 and outputted to display unit 16 with the patient information and imaging condition. Here, the function restriction flag is set in function restriction unit 15*b* as described above, so that the display of a portion of the radiological examination information to be displayed on display unit 16 is restricted by function restriction unit 15*b* (S28).

More specifically, in the present embodiment, a radiation image for use in radiology reading is restricted and controlled not to be displayed since the image shows details of disease and may lead to the leakage of personal information. The imaging condition is displayed on display unit 16 without display restriction since it is information required for the operator to perform next imaging, while the patient information which may lead to serious leakage of personal information is restricted and controlled not to be displayed on display unit 16.

In the mean time, if it is determined that the function restriction flag is reset by function restriction unit 15*b* in step S20, that is, console 10 is determined to be in the radiation imaging room or radiation imaging preparation room, all items of radiological examination information shown in FIG. 6 are displayed on display unit 16 of console 10 after imaging for a positioning verification image is performed (S30).

Then, main imaging is performed in the same manner as that described above and a radiation image signal for use in radiology reading is stored in radiation image storage unit 14 of console 10 (S34). Thereafter, the radiation image signal for use in radiology reading will be read out by control unit 15 and outputted to display unit 16 with the patient information and imaging condition. In this case, the function restriction flag is reset in function restriction unit 15*b*, as described above, so that display restriction is not imposed by function restriction unit 15*b* and the radiation image for use in radiology reading is displayed on display unit 16 with the imaging condition and patient information (S36).

In the embodiment described above, an arrangement may be adopted in which, while such display restriction as described above is imposed, a release instruction is inputted by the operator from input unit 17 of console 10 and the display restriction is released in response to the release instruction after it is confirmed by the operator that no person is around. Preferably, the input of release instruction is allowed only when an authentication procedure, such as input of ID card or password, biometric authentication, or the like, is successfully performed.

In the embodiment described above, radiation image for use in radiology reading and personal information of a patient are the subject of display restriction, but display restriction items are not limited to these and may be set arbitrarily in advance.

For example, with respect to the display of radiation images, only a most recently obtained radiation image is allowed to be displayed while display of a radiation image obtained before that is restricted. The most recently obtained radiation image is allowed to be displayed as it is a positioning verification image, while display of a radiation image obtained before that is restricted as it includes personal information and unnecessary display of the image may lead to leakage of the personal information. Radiation images obtained in the past are those stored, for example, in radiation image storage unit 14 of console 10, in a server linked to console 10 through a network, or the like. When, for example, the positioning in the imaging performed in the past needs to be verified, a low resolution image is sufficient for that purpose, so that a radiation image obtained in the past may also be displayed after being converted to a low resolution image.

In the embodiment described above, display of the radiological examination information is restricted when the function restriction flag is set in function restriction unit 15*b*, but the restriction is not limited to the display of radiological examination information and, for example, rewriting of patient information registered in patient information management unit 12 of console 10 may be restricted. Where imaging implementation information to be obtained after imaging of a radiation image is actually performed is registered with patient information, the rewriting of patient information is restricted as described above, but the imaging implementation information may be made rewritable. The imaging implementation information may include, for example, a tube voltage at the time of imaging the radiation image, mAs value, setup SID, a number of obtained radiation images, exposure time of radiation, and the like. The setup SID refers to the distance between radiation source 30 and radiation image detector 20 when imaging of a radiation image is performed. The tube voltage, mAs value, and the like are obtained when, for example, an AEC (Auto Exposure Control) is performed.

It is also possible to estimate an amount of radiation exposure for a patient from the exposure result of AEC and the amount of radiation exposure may sometimes be stored, as radiological examination information, in relation to the patient information and radiation image. In such a case, when a cumulative value of radiation exposure is displayed in console 10, the display of cumulative value may be restricted in a visiting medical site as it is information desired not to be seen by a third person. In a radiation imaging room, on the other hand, the display is not restricted as the cumulative value of radiation exposure is required for determining an imaging condition before heading to a visiting medical site.

Further, in the embodiment described above, administrator registration server 40 installed in the radiation imaging room or radiation imaging preparation room is used as the access point for console 10 to obtain location information, but the access point is not limited to this and an access point may be provided in the radiation imaging room, radiation imaging preparation room, corridor, and each patient room which are linked to a LAN (Local Area Network) of the hospital. Then, for example, each access point may be given ID information, and location information may be obtained by dynamically selecting ID information of an access point having a best communication status with console 10.

Still further, in the embodiment described above, location of console 10 is obtained based on a communication status with an administrator registration server 40, but the location information is not limited to this and, for example, the quantity of radiation detection cassette communicatable with console 10 through wireless communication may be used as the location information.

Figure 9:
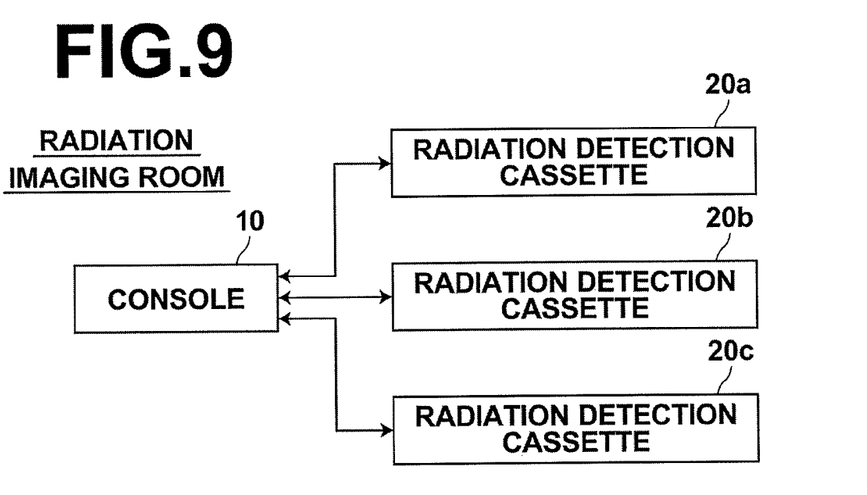
FIG. 9 illustrates the relationship between the counts of console and cassette in a radiation imaging room.

That is, it is often the case that a plurality of radiation detection cassettes 20a to 20c is housed in a cradle, for example, in the radiation imaging room or radiation imaging preparation room, as illustrated in FIG. 9. In the case where console 10 is placed in the radiation imaging room or radiation imaging preparation room, console 10 may perform wireless communication with the plurality of radiation detection cassettes 20a to 20c. On the other hand, in the case where console 10 is in a patient room for visiting radiation imaging, the quantity of radiation detection cassette communicatable with console 10, through wireless communication, is only one used for the visiting radiation imaging.

By making use of such situation, the quantity of radiation detection cassette communicatable with console 10 through wireless communication may be obtained as the location information. If the quantity obtained is one, console 10 may be determined to be in a place, such as patient room, other than the radiation imaging room or radiation imaging preparation room. If the quantity obtained is plural, console 10 may be determined to be in the radiation imaging room or radiation imaging preparation room. Note that when such method is used, the communicatable distance between console 10 and radiation detection cassette is limited to a certain value that allows the determination of the location of console 10.

Further, instead of obtaining the quantity of radiation detection cassette communicatable with console 10 through wireless communication as the location information, as described above, type information of radiation detection cassette may be obtained and the type information may be used as the location information. For example, if a radiation detection cassette is provided in a built-in fashion, the information is obtained as the location information and console 10 may be determined to be in the radiation imaging room. If the radiation detection cassette is a cassette dedicated to visiting radiation imaging, the information may be obtained as the location information, and console 10 may be determined to be in a place, such as a patient room, other than the radiation imaging room.

The types of radiation detection cassettes may be set in radiation detection cassettes in advance and obtained by console 10 through wireless communication or they may be inputted in console 10 by the operator using input unit 17. Further, a radiation cassette for visiting radiation imaging may sometimes be given a specific ID, and the ID may be obtained as a type of the radiation detection cassette.

Figure 10:
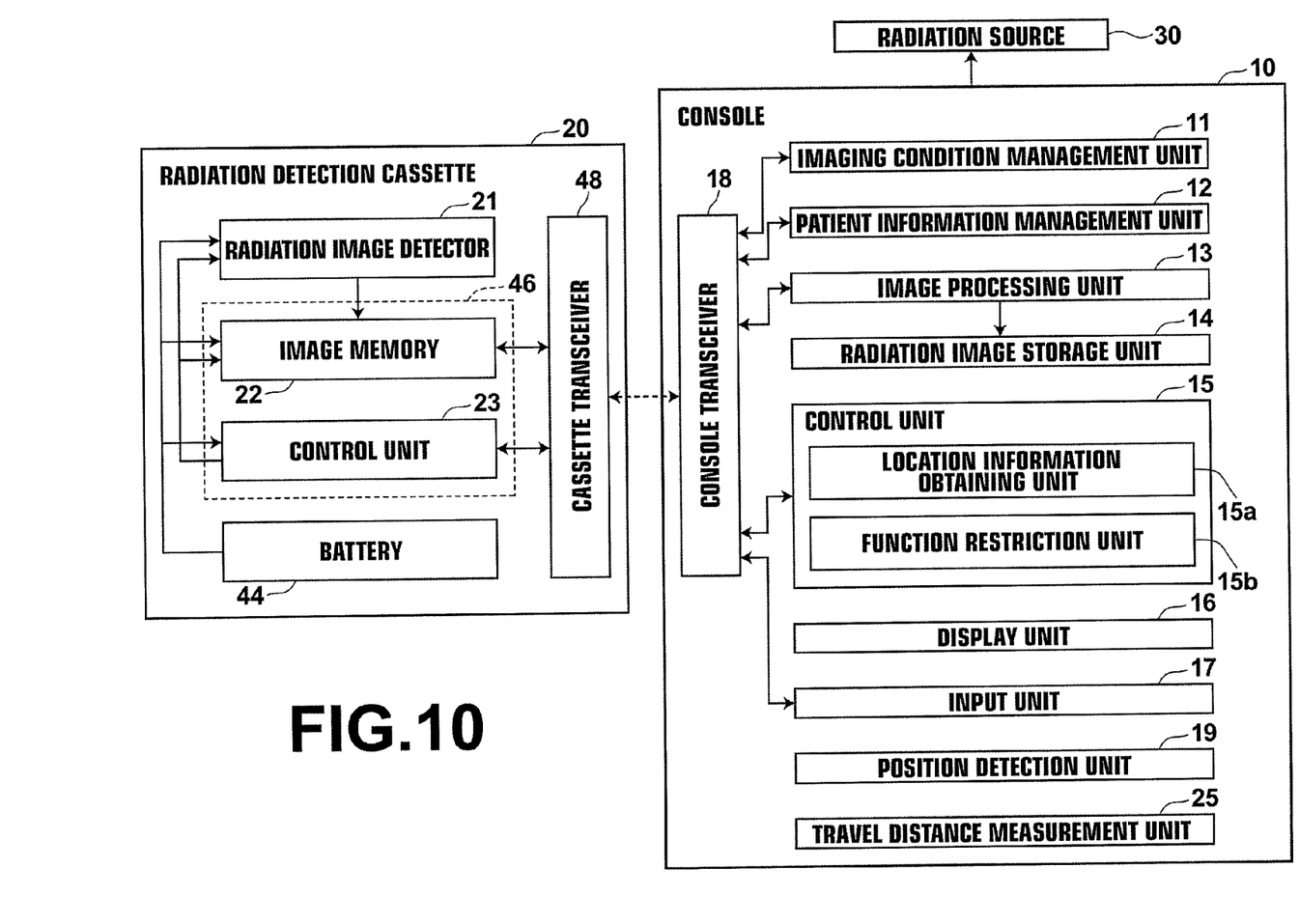
FIG. 10 is a block diagram of a radiation image taking system that employs another embodiment of the radiation imaging control apparatus of the present invention.

Further, as shown in FIG. 10, position detection unit 19 for detecting a location of console 10 may be provided in console 10 and the location detected by position detection unit 19 is obtained as the location information. Position detection unit 19 may obtain a location of console 10 by, for example, communicating with an access point described above or using any known position detection system, such as GPS.

The location detection is not necessarily performed constantly by position detection unit 19, and it is preferable that the detection is performed in the case where a travel distance measured by travel distance measurement unit 25 shown in FIG. 10 becomes greater than or equal to a predetermined value. As for travel distance measurement unit 25, for example, an acceleration sensor or a rotary encoder for detecting rotations of wheels 10d of console 10 may be used. Further, if console 10 is driven by a battery and wheels 10d are moved electrically, the travel distance may be measured by monitoring the remaining battery level.

Further, for example, an ID card or RFID card, tied to a wire so as not to be stolen, provided in a radiation imaging room, radiation imaging preparation room, or nurses' station may be inserted into console 10 or matched to read out ID information recorded on the card and obtain the ID information as the location information, whereby console 10 may be determined to be in the radiation imaging room or the like. In this case, the relationship between the ID information and location is set in console 10 in advance. In the case of ID card, console 10 may be determined to be in a place other than the radiation imaging room or the like when removal of the ID card from console 10 is detected, and a part of a function of console 10 may be restricted. In the case of RFID card, console 10 may be determined to be in a place other than the radiation imaging room or the like in the case where the travel distance of console 10 from the time when the ID information is matched becomes greater than or equal to a predetermined value, and a part of the function of console 10 may be restricted.

What is claimed is:

1. An operation control method for a radiation imaging control apparatus which is constructed movably and includes a control unit for receiving a predefined operational instruction for radiation imaging to output a control signal for the radiation imaging according to the received operational instruction and a display unit for displaying radiological examination information, wherein:
    the apparatus obtains location information capable of identifying a location of the apparatus; and
    a part of a function of the apparatus is restricted if the location identified by the obtained location information is a location other than a predetermined location.

2. A radiation imaging control apparatus which is constructed movably and includes a control unit for receiving a predefined operational instruction for radiation imaging to output a control signal for the radiation imaging according to the received operational instruction and a display unit for displaying radiological examination information, wherein the apparatus comprises:
    a location information obtaining unit for obtaining location information capable of identifying a location of the apparatus; and
    a function restriction unit for restricting a part of a function of the apparatus if the location identified by the location information obtained by the location information obtaining unit is a location other than a predetermined location.

3. The apparatus of claim 2, wherein the location information obtaining unit is a unit that performs wireless communication with a predetermined access point and obtains a communication status of the wireless communication as the location information.

4. The apparatus of claim 2, wherein the location information obtaining unit is a unit that receives the control signal outputted from the control unit and obtains type information for a radiation image detector that detects a radiation image.

5. The apparatus of claim 2, wherein the location information obtaining unit is a unit that receives the control signal outputted from the control unit and obtains quantity information for a radiation image detector that detects a radiation image.

6. The apparatus of claim 2, wherein the apparatus comprises a position detection unit for detecting a location of the apparatus and the location information obtaining unit is a unit that obtains the location detected by the position detection unit as the location information.

7. The apparatus of claim 6, wherein the apparatus comprises a travel distance information obtaining unit for obtaining a travel distance of the apparatus and the position detection unit is a unit that performs the detection of a location of the apparatus in the case where the travel distance becomes greater than or equal to a predetermined value.

8. The apparatus of claim 2, wherein the function restriction unit is a unit that restricts display of a portion of the radiological examination information to be displayed on the display unit.

9. The apparatus of claim 8, wherein the function restriction unit is a unit that restricts display of information related to personal information included in the radiological examination information to be displayed on the display unit.

10. The apparatus of claim 8, wherein the function restriction unit is a unit that restricts display of a radiation image included in the radiological examination information to be displayed on the display unit.

11. The apparatus of claim 10, wherein the function restriction unit is a unit that restricts display of a radiation image for use in radiology reading included in the radiological examination information to be displayed on the display unit.

12. The apparatus of claim 10, wherein the function restriction unit is a unit that restricts display of a radiation image obtained in the past included in the radiological examination information to be displayed on the display unit.

13. The apparatus of claim 10, wherein the function restriction unit is a unit that restricts display of a radiation image included in the radiological examination information to be displayed on the display unit other than a most recently obtained radiation image.

14. A radiation image taking system, comprising:
the radiation imaging control apparatus of claim 2;
a radiation source for emitting radiation based on a control signal outputted from the radiation imaging control apparatus; and
a radiation image detector for receiving radiation emitted from the radiation source and transmitted through a subject to detect a radiation image,
wherein the apparatus is constructed movably.

* * * * *